United States Patent [19]

Braig et al.

[11] Patent Number: 4,586,026

[45] Date of Patent: Apr. 29, 1986

[54] INFRARED GAS ANALYZER USING COUNT QUADRATURE SAMPLING

[75] Inventors: James R. Braig, Santa Ana; Max D. Liston, Irvine, both of Calif.

[73] Assignee: Liston Edwards, Inc., Newport Beach, Calif.

[21] Appl. No.: 549,411

[22] Filed: Nov. 7, 1983

[51] Int. Cl.⁴ .............................................. H03K 13/00
[52] U.S. Cl. .............................. 340/347 AD; 250/343; 250/565
[58] Field of Search ................. 340/347 AD, 347 SH; 250/338–343, 564–565; 356/51

[56] References Cited

U.S. PATENT DOCUMENTS

| | | | |
|---|---|---|---|
| 3,745,349 | 7/1973 | Liston | 250/565 |
| 4,027,972 | 6/1977 | Davies | 250/343 |
| 4,061,918 | 12/1977 | Preier et al. | 250/343 |
| 4,079,256 | 3/1978 | Ford et al. | 250/343 |
| 4,390,785 | 6/1983 | Faulhaber et al. | 250/338 GA |
| 4,420,742 | 12/1983 | Tadauchi et al. | 340/347 AD |
| 4,441,096 | 4/1984 | Evanchuk | 340/347 AD |
| 4,445,111 | 4/1984 | Suift et al. | 340/347 AD |
| 4,496,937 | 1/1985 | Kitagawa et al. | 340/347 SH |

Primary Examiner—Vit W. Miska
Attorney, Agent, or Firm—George F. Bethel; Patience K. Bethel

[57] ABSTRACT

The percentage gas concentration within a sample as measured in a conventional optical bench is derived from the composite signal of the reference beam and sample beam transmitted through a sample cell in the optical bench. The primary source, which generates the reference beam and the secondary source which generates the sample beam are driven ninety degrees out of phase. The composite signal derived from the detector in the optical bench is digitized and then integrated according to the quadrature of the primary component of the composite signal derived from the reference beam, and is also integrated according to the quadrature of the secondary component of the composite signal derived from the sample beam. What is obtained is the integral of the absolute value of the secondary component and the integral of the absolute value of the primary component of the composite signal over one cycle of the reference beam and sample beam. The ratio of these component signals is computed to obtain a signal which is related to the percentage concentration of reference gas contained within the sample.

10 Claims, 4 Drawing Figures

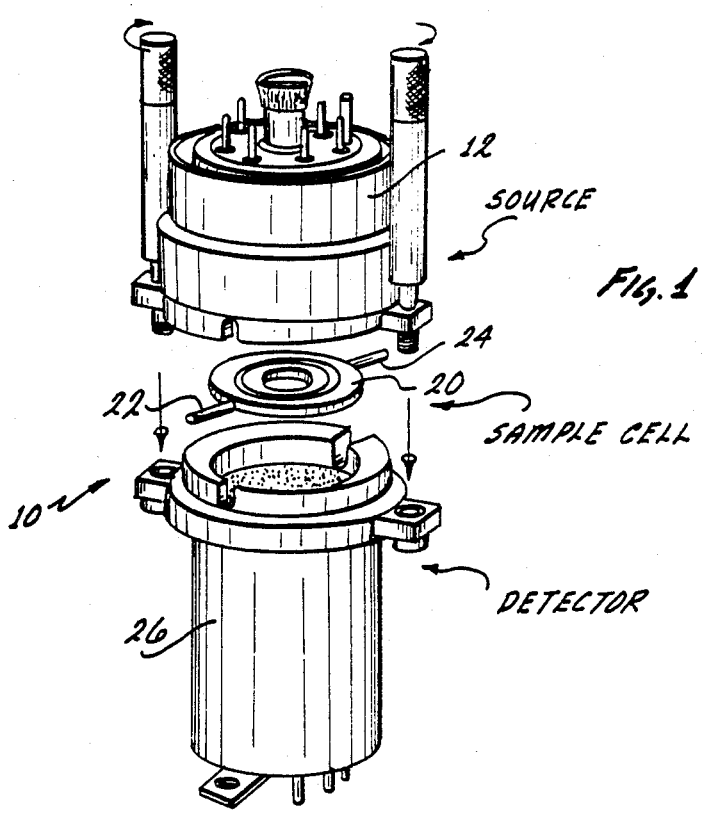
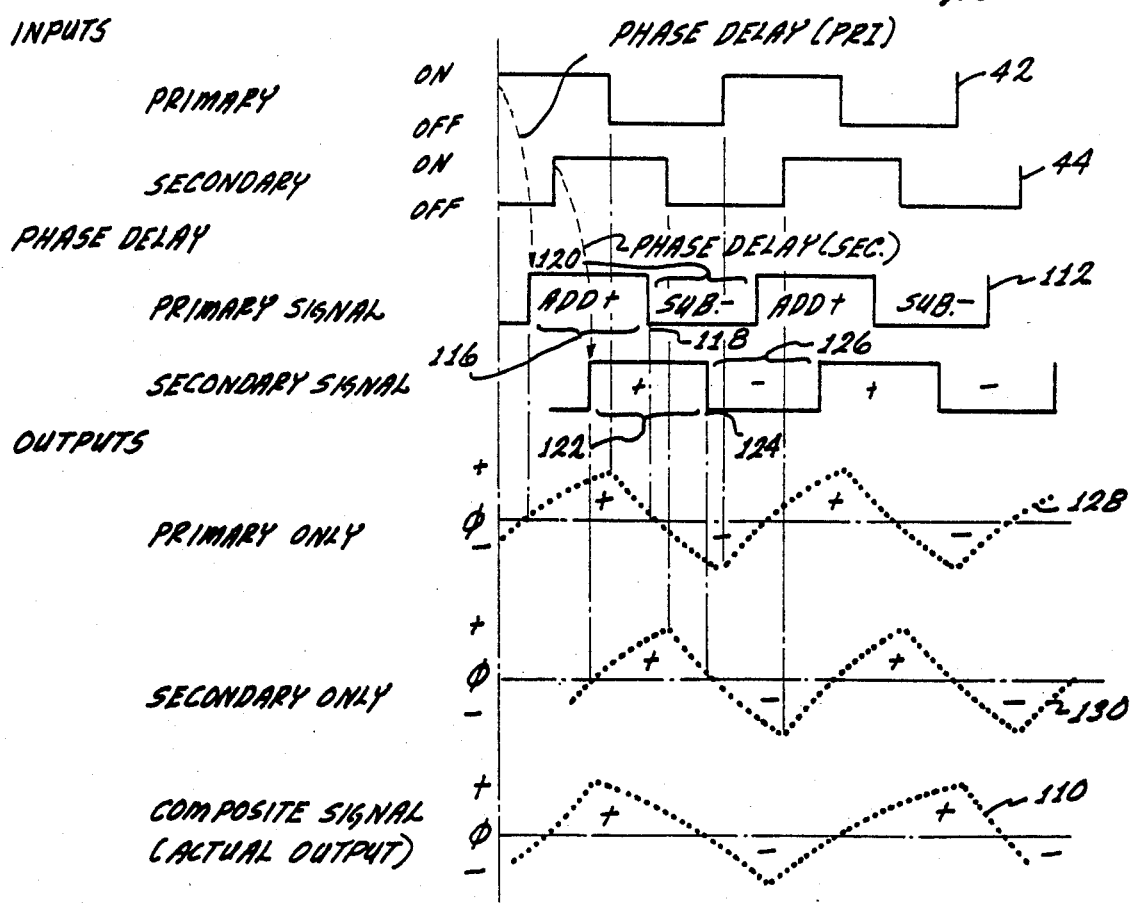

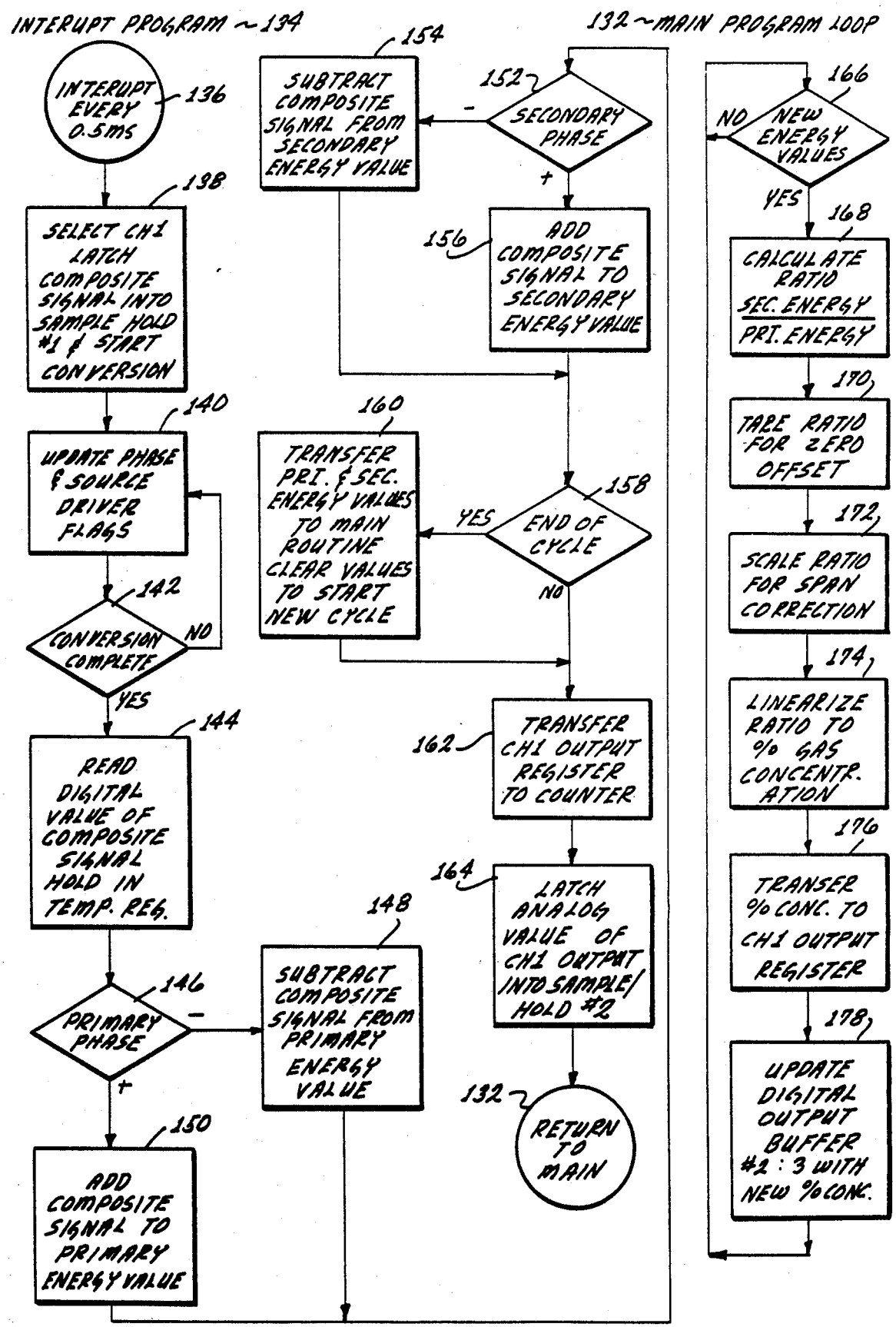

INFRARED GAS ANALYZER USING COUNT QUADRATURE SAMPLING

BACKGROUND OF THE INVENTION

1. Field of the Invention

The present invention relates to the field of radiant energy analyzers and more particularly, to a dual source, common mode rejection radiant energy analyzer.

2. Description of the Prior Art

Infrared or radiant energy analyzers are well known electronic systems for measurement of the absorption of energy from the radiant energy beam by a sample gas. Prior art analyzers have generally been characterized as double beam-in-space or double beam-in-time instruments. A double beam-in-space instrument is an optical system in which a reference beam is used which does not traverse the sample cell. A double beam-in-time instrument is an optical system in which the sample and reference beam, which are compared to compute the percentage concentration of a specified gas, both traverse the sample cell.

Typically, such double beam-in-time or single path dual wave length instruments involve various types of mechanical filter wheels, or rotating or reciprocating mirrors subject to mechanical failure, misalignment and degradation in performance from dirt and other substances. These susceptabilities of electromechanical infrared gas analyzers result in erroneous responses to mixtures of gaseous substances which are not uniformly distributed throughout the sample cell. In addition, the infrared analyzer itself is difficult to manufacture in large quantities. In essence, the electrooptical system and detectors of such prior systems require a large amount of bench calibration and customized adjustment.

In response to shortcomings of these prior art devices, the assignee of the present invention developed an improved infrared analyzer as described in greater detail in U.S. Pat. No. 3,745,349. In that analyzer the fine structure of the infrared absorption spectrum at a predetermined gas contained within a reference cell is compared to the fine structure of the infrared absorption spectrum obtained from the gas contained within a sample cell. An optical bench, such as shown and described below in connection with FIG. 1, is used to generate the infrared energy used for measurement and to transmit the infrared energy through the sample gas to a detector.

A primary infrared source is positioned behind the reference cell containing the reference gas. A secondary infrared source is positioned on the opposing side of the reference gas cell and between the reference gas cell and a sample gas cell. An infrared detector is then positioned on the opposing side of the sample gas cell so that the primary infrared source, the reference gas cell, the secondary infrared source, sample gas cell and the detector form a linear optical chain in that order. The infrared sources which are used are identical to each other, and are described in greater detail in U.S. Pat. No. 4,084,096 assigned to the same assignee of the present invention.

The primary and secondary infrared sources are energized in this prior art device one hundred and eighty degrees out of phase with respect to each other to effect chopped radiation transmission to the infrared detector. Energy from the primary infrared source passes through the reference cell which acts as a filter, past the secondary infrared source, through the sample cell and into the detector. Once energy from the primary source reaches the sample cell, the amount of reference gas included within the sample cell has practically no effect on the intensity of the beam from the primary source since the reference cell has filtered or absorbed substantially all of the indentifying frequencies from its spectrum. The primary energy path is referred to as the reference beam. The primary infrared source then turns off and the secondary source turns on. Energy from a secondary source passes directly through the sample cell into the detector. The amount of reference gas in a sample cell now significantly affects the energy impinging on the detector from the secondary source. The higher the concentration of the reference type of gas in the sample cell, the lesser the amount of energy from the secondary source that reaches the detector. This beam is called the sample beam.

In this type of optical bench dirt and other optical irregularities in the same cell affect or modulate the reference and sample beam to the same degree, inasmuch as the optical path, beginning at the sample cell, is identical for both the reference and sample beams. The difference in modulation between the reference beam and sample beam accounts for the analyzer's sensitivity to the reference gas.

An analog signal from the detector, which is a composite signal corresponding to the reference and sample beams is preamplified and shaped for input to a phase demodulator. During a first 180 degree phase period, the output of the demodulator alternates between an analog signal proportionate to the reference beam, and during the subsequent 180 degree phase period an analog signal proportionate to the inverse of the sample beam. When these analog signals are then integrated over time in an analog integrator circuit, the signal corresponding to the reference beam is subtracted from the signal corresponding to the sample beam and averaged over time. The output of the integrator is coupled to a servo-control circuit which is used to drive the secondary infrared source in a direction to null the output of the integrator. The amount of servo-drive used to null the integrated difference between the reference and sample beam is then read out as the relative output of the optical bench. This servo-output is then linearized and calibrated for a gain adjustment to produce an analog output representative of the percentage of reference gas in the sample cell.

While this prior art device represents a substantial improvement over infrared analyzers previously available, it still suffers from the drawback that the response times are slow and only an analog output is available. A large amount of fine tuning is required during production in order to adjust the servo-system, its calibration and linearization. The system is further characterized by a significant thermal drift or warmup period. The design is difficult to adapt to different operating formats and tends to be limited to the hardware implementation and performance of the basic design.

What is needed then is an infrared absorption analyzer which is not subject to the disadvantages of prior art analyzers as just enumerated. Such an analyzer should provide fast response times with extremely accurate digital outputs. The design should be adapted for mass production requiring little if any fine tuning or bench testing or calibration during production. The design should also be characterized by stable operation and not subject to thermal drifts or sensitivity to ambient conditions. Finally, the design must be one which is highly flexible so that the design can be easily configured in a plurality of output, control and performance configurations from the same basic design unit.

BRIEF SUMMARY OF THE INVENTION

The invention is an apparatus for use in combination with an optical bench for generating an analog composite signal. The analog composite signal is comprised of a primary component derived from a reference beam generated by a primary source and a secondary component derived from a sample beam generated by a secondary source. The apparatus comprises a first circuit for digitizing the analog composite signal. A second circuit demodulates the digitized composite signal into a digitized primary component and digitized secondary component. A third circuit generates the ratio of a measure of the secondary component to the primary component, namely, the integral over the cycle of the absolute value of the secondary component on one hand and of the primary component on the other hand. By reason of these elements, common mode rejection is obtained within a composite signal when the signal is processed in digital format.

More particularly, the invention comprises a circuit for use in combination with a radiant energy analyzer for digitizing an analog composite signal generated by the radiant energy analyzer. The circuit comprises a comparator having one input coupled to the analog composite signal. A counter generates a digital count and is coupled to the comparator. The counter is incremented and decremented according to the output of the comparator. A digital-to-analog converter is coupled to the output of the counter and in turn has its output coupled to the second input of the comparator. The contents of the counter are thus revised until a null output of the comparator is obtained at which time the counter contents are substantially equal to the digitized value of the analog composite signal which is provided as an input to the comparator.

The reference beam from the primary source is periodically generated as is the sample beam from the secondary source. The analog composite signal generated from the reference and sample beams is comprised of the primary and secondary components derived from exposure of the sample to the reference beam and sample beam. The primary component corresponds to the exposure of the sample to the reference beam and the secondary component corresponds to exposure of sample to the sample beam. Periodic generation of the reference and sample beams are phase shifted with respect to each other by approximately ninety degrees so that the primary and secondary components of the composite signal are similarly phase shifted with respect to each other by approximately 90 degrees. After digitization by the circuit set forth above, the composite signal is integrated according to the quadrature of one of the primary and secondary components to obtain the integral of the absolute value of the one component. The integral of the absolute value of the other one of the primary and secondary components is then derived. The ratio of the integrals of the absolute value of the secondary to the integral of the absolute value of the primary component is then computed within a microprocessor. By the combination of these methodology steps in connection with the circuit described, extremely fast and accurate percentage concentrations of the energy absorbing substance is determined by exposure to the reference beam and sample beam and calculated in the manner characterized by common mode rejection.

More particularly, the steps of periodically generating the reference beam, periodically generating the sample beam, integrating the composite signal according to the quadrature of one of the primary and secondary components of the composite signal, deriving the integral absolute value of the other one of the primary and secondary components of the composite signal, and generating the ratio of the integral of the absolute value of the secondary component to the integral of the absolute value of the primary component are each performed in a microprocessor. The steps of digitizing the analog composite signal is performed within a D/A-−A/D convertor which is in communication with the microprocessor. The reference beam and sample beams are produced in an optical bench coupled to the D/A-−A/D convertor and are controlled by the microprocessor.

The invention and its illustrated embodiment is better understood by considering the embodiment as depicted in the following drawings.

BRIEF DESCRIPTION OF THE DRAWINGS

The invention will be more clearly understood by reference to the description below taken in conjunction with the accompanying drawings wherein:

FIG. 1 is an exploded perspective pictorial view of an optical bench used in conjunction with the invention;

FIG. 3 is a timing diagram as illustrated in the operation of the invention; and, FIG. 4 is a flow diagram of the operation of the circuit of FIG. 2 which results in the timing diagram of FIG. 3.

Figure 2:
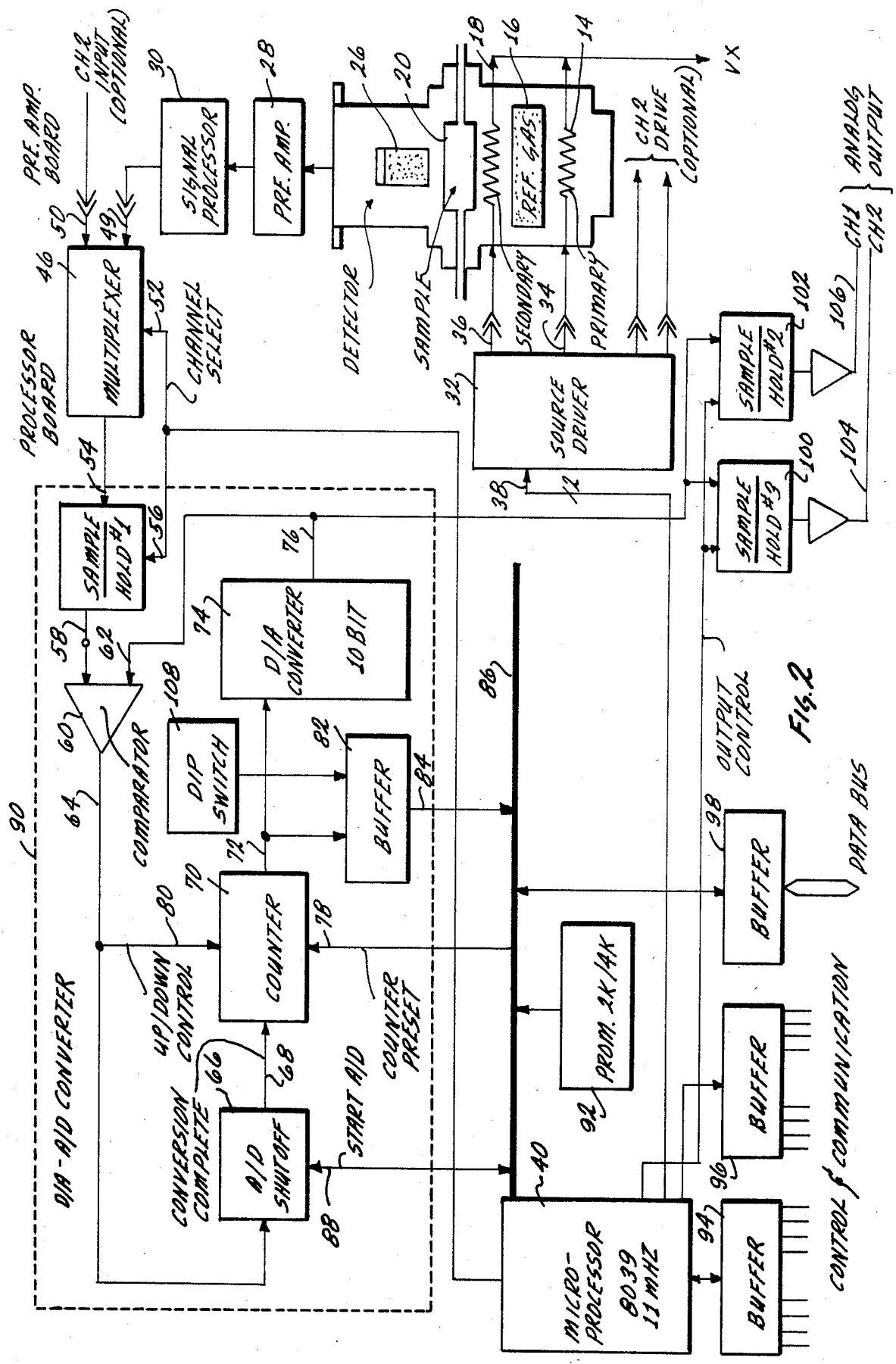
FIG. 2 is a schematic diagram of the circuitry of the invention.

The invention and its various embodiments can be better understood by considering the above Figures in light of the following detailed description.

DETAILED DESCRIPTION OF THE PREFERRED EMBODIMENTS

The invention is an infrared absoption analyzer having a single optical path for a reference beam and sample beam through a sample cell wherein the reference beam is generated by a primary infrared source during a ninety degree phase period. The sample beam is generated by a secondary infrared source during a subsequent ninety degree phase period. The power levels of the primary and secondary sources are held constant throughout the measurement. The reference and sample beams impinge upon a detector after traversing the sample cell in response to which the detector produces an analog output. The analog output is converted to digital form, and a ratio of the secondary to primary energy is digitally calculated. The numeric ratio is then used to compute the percentage of the reference gas in the sample cell.

The operation of the invention and the means for its implementation can be better understood by now turning to the Figures. FIG. 1 is an exploded pictorial perspective of an optical bench, generally denoted by reference numeral 10. The optical bench 10 is substantially identical to prior art optical benches such as describe in connection with U.S. Pat. No. 3,745,349 and sold by Liston Edwards, Inc. of Newport Beach, Calif. as Model 1050 Optical Bench. Optical bench 10 includes a source 12 shown in the upper portion of FIG. 1. Source 12 in turn includes a primary source 14 of infrared energy diagramatically depicted in FIG. 2. Also included is a reference gas cell 16 containing an arbitrary selected reference gas, such as carbon dioxide. On the opposing side of reference gas cell 16 also included within source 12 is a secondary source 18 of infrared energy. Again, as diagramatically depicted in FIG. 2, on the opposing side of source 12, which includes primary source 14, secondary source 18 and reference gas cell 16, is a sample gas cell 20 which is also shown in exploded view in FIG. 1.

The sample gas to be tested is circulated from inlet 22 into sample cell 20 and then outwardly through outlet 24 according to conventional means. As shown in FIG. 1, a detector 26 is disposed on the opposing side of sample cell 20 so that sample cell 20 is sandwiched between source 12 and detector 26. Turning again to FIG. 2, detector 26 is diagramatically depicted on the opposing side of sample cell 20 and has its output coupled to a conventional analog preamplifier 28. Preamplifier 28 in turn has its output coupled to the input of a conventional signal processor 30. Typically, preamplifier 28 is a charge amplifier or electrometer, which is well known to the art. The current produced by a fluctuating capacitor within detector 26 is converted to a low impedance voltage signal by preamplifier 28. Signal processor 30 following preamplifier 28 is a band pass filter which removes all interference not centered at the frequency at which primary secondary sources 14 and 18 respectively are modulated as described below.

Turn now to FIG. 2 wherein primary source 14 and secondary source 18 are coupled to and driven by a source driver 32. Source driver 32 bears a conventional voltage driver wherein primary output 34 and secondary output 36 of source driver 32, coupled respectively to primary infrared source 14 and secondary infrared source 18, are responsively driven according to the corresponding inputs 38 which are coupled to source driver 32. In the illustrated embodiment, source driver 32 includes a plurality of Darlington pairs providing a plurality of outputs in response to a corresponding plurality of inputs 38. Inputs 38 in turn are coupled to microprocessor 40 which is described in greater detail below.

Turning to FIG. 3, the voltage and power signal applied to primary infrared source 14 is illustrated by line 42. The voltage and power signal provided to secondary infrared source 18 is illustrated by line 44. As shown, a square wave driving signal is applied to each infrared source with a frequency chosen according to design optimization, in this case approximately 18 Herz. Clearly, the optimal design is determined according to the characteristic responses of sources 14 and 18 and detector 26, as well as the time period during which any change in the sample gas is expected to occur. The power applied to primary and secondary sources 14 and 18 respectively and as illustrated in FIG. 3 by lines 42 and 44, is particularly characterized as a beam of composite signals which are phase shifted one with respect to the other by 90 degrees. The significance and the manner in which the 90 degree phase shift or quadrature is used in the invention will be understood and described in greater detail below after the circuitry of FIG. 2 has been completely described.

Turn again now to FIG. 2. The analog output of signal processor 30 is coupled to a conventional multiplexer 46. In the illustrated embodiment, multiplexer 46 is indicated as having two input channels, channel 48 coupled to signal processor 30 and channel 50 coupled to a second optical bench, preamplifier and signal processor which is not illustrated. Multiplexer 46 is shown simply to illustrate the power of the invention wherein a multiplicity of optical benches can be controlled and measured by a single master circuit. Multiplexer 46 selects between channels 48 and 50 in response to the input at a channel select 52. Channel select input 52 in turn is coupled to microprocessor 40 and is activated according to conventional software control described in greater detail in connection with FIG. 4.

The output of multiplexer 46 is coupled to a sample and hold circuit 48 which samples the analog output of multiplexer 46 and holds that value which is present at its input 54 when sample hold circuit 48 is enabled by the channel select signal provided at input 56. Again, the channel select signal provided at input 56 is generated and coupled thereto by microprocessor 40. Therefore, when channel 49 or 50 is selected, the value then coupled through multiplexer 46 will be sampled and held within circuit 48. Sample and hold circuit 48 is conventional and well known to the art and is sold by Precision Monolithics of Sunnyvale, Calif. as Sample Hold Circuit SMP 11GY.

The analog signal held at the output 58 of sample hold circuit 48 is compared in comparator 60 to the signal at input 62 of comparator 60. However, the analog signal at input 62 is generated by a separate loop as described as follows. Output 64 of comparator 60 is coupled to an input of an analog-to-digital convertor 66. Output 68 of convertor 66 is a counter start/stop signal which enables a digital counter 70. Counter 70 begins counting when enabled by the counter start/stop signal from the output 68 of the convertor 66 and counts up or down as determined by the sign of the output 64 of comparator 60. Output 72 of counter 70 is coupled to a ten bit digital-to-analog convertor 74. The contents of counter 70 are thus reconverted to analog form at output 76 and fed back to input 62 of analog comparator 60.

Counter 70 is preloaded pursuant to microprocessor control by a digital preset signal provided through input 78 of counter 70. Microprocessor 40 will choose a counter preset value which will be approximately equal to the expected last value, or best guess of the voltage being measured. When initiated, a preset value 70 is provided at output 72 of counter 70, converted into analog form 76 and compared within comparator 60 to the analog signal held by sample and hold circuit 48. If the value in counter 70 is greater than the value held within sample and hold circuit 48, output 64 of comparator 60, which is coupled to up/down control input 80 of counter 70, will cause counter 70 to count down.

The circuit 90 also includes a dual-in-line input switch 108 which provides a digital number to buffer 82 for coupling to bus 86. Therefore, by manual activation of switch 108, a predetermined value can be loaded into buffer 82 to modify, control or initialize the operation of microprocessor 40.

Ultimately, the contents of counter 70 will reach a digital value equal to the analog value of the voltage at output 58 of sample and hold circuit 48. When this occurs, the output of comparator 60 will be essentially zero, thereby causing analog-to-digital shut-off circuitry 66 to disable counter 70. The equalized or digitized value then contained within counter 70 is available at output 72 and is latched into a buffer 82. The output 84 of buffer 82 in turn is coupled to a bus 86 coupled to microprocessor 40. Analog-to-digital converter 66 in turn is controlled by a start A-to-D signal on terminal 88 supplied from microprocessor 40 according to software control through bus 86. Similarly the counter preset signal described above in connection with input 78 of counter 70 is similarly microprocessor derived through bus 86.

Therefore, the circuitry generally shown and described as the D/A—A/D convertor 90 forms an analog-to-digital sample and hold convertor which in effect digitizes the analog signal from the selected optical bench and presents the digitized signal to bus 86 for further processing as described in FIG. 4.

The use of microprocessor 40 as the controlling circuit within the overall system illustrated in FIG. 2 allows for inherent flexibility to configure the basic circuit design in any one of a plurality of output formats required by the user. The software program for operation of the circuit of FIG. 2 is stored within programmable read only memory 92 and coupled in a conventional manner to microprocessor 40 through bus 86. Similarly, input-output buffers 94 and 96 are coupled to the input-output ports of microprocessor 40 to provide control by and communication with the user. Typically, such control and communication is effected through a plurality of switches often configured in the form of a keyboard touchpad and a digital and numeric/digital display (not shown).

Similarly, a digital buffer 98 directly communicates with bus 86 to provide a means for direct data access to operations occuring on bus 86 within the circuitry of FIG. 2. Thus, according to conventional design principles, microprocessor 40 and its operation can be slaved or coordinated to other processing units or other peripherals. Thus, if desired, in addition to providing a real-time digital display, microprocessor 40 may communicate through buffer 98 to a hard copy printer or a tape drive to provide an archival record.

Finally, sample and hold circuits 100 and 102 are coupled to microprocessor 40 and selectively enabled, with a number loaded into counter 70 from processor 40, thereby to provide an analog output from output 76 of digital-to-analog convertor 74 if desired by the user through buffered outputs 104 and 106 respectively. Therefore, both a digitized value of the precentage of gas detected within sample cell 20 and an analog signal proportional to gas concentration is easily provided by the architecture of the circuitry shown in FIG. 2.

Turn now to FIG. 3 wherein the operation of the circuitry of FIG. 2 can now be understood as implemented through the software control as described in connection with FIG. 4. A composite signal from detector 26 is alternately provided to the input 54 of sample and hold circuit 48 as represented by line 110 of FIG. 3. Composite signal 110 is the algebraic sum of the signal produced and detected at 26 from primary source 14 and secondary source 18 when driven by the voltages illustrated by lines 42 and 44 of FIG. 3, which in turn are software originated. Composite signal 10 thus includes both the primary and secondary source originated signals from detector 26. Primary source 14 and secondary source 18 are driven with an orthogonal phase difference or quadrature in order to facilitate demodulation of the two signals from detector 26. Signals which are thus linearly superimposed as described do not interact and can be later separated. While a phase shift of 90 degrees between perfectly symmetric or sinusoidal waveforms will allow exact separation of the primary and secondary components, an approximate phase shift of 80 degrees of approximately sinusoidal waveforms will still allow for acceptable separation and results according to the invention. Naturally, the greater the quadrature departs from 90 degrees and the greater the waveforms depart from antisymmetric form, the less accurate are the measured results.

Each dot of line 110 of FIG. 3 which represents the composite signal, symbolically represents a sample and hold cycle executed as described in connection with FIG. 2. However, the composite signal arriving at input 54 of sample and hold circuit 48 is necessarily phase shifted or delayed in time from the driving signals applied to primary source 14 and secondary source 18. Microprocessor 40 compensates for the time delay of the sources, detector and processing circuitry up to input 54 by internally generating phase shifted signals represented by lines 112 and 114 corresponding respectively to power signals 42 and 44.

Line 112 represents the timing intervals of the phase shifted primary portion of the composite signal arriving at input 54 while line 114 represents the timing intervals of the phase shifted secondary portion of the composite signal arriving at input 54. Therefore, the primary contribution to the composite signal during interval 116 of primary phase portion 112 must be positive, have a zero crossing at point 118 and go negative during interval 120. Microprocessor 40 assumes this to be the case, since it knows how it has driven primary source 14, knows the time delay from the sources and the detector to input 54 and therefore can expect to see an output corresponding to the primary source having a periodicity covering intervals 116 and 120, going positive in interval 116 and going negative in interval 120. Similarly, secondary phase portion 114 includes an interval 122 during which the secondary contribution to the composite signal must be positive going with a zero crossing at point 124 and is negative going during interval 126. Therefore, the absolute value of the composite signal is integrated through intervals 116 and 120, which correspond to a single cycle, and the secondary contribution will cancel out, leaving a value corresponding to the primary contribution only. This will be true, provided that the primary contribution to the intervals 116 and 120 is antisymmetric. In other words, during interval 122 half of the value of the secondary signal will be added to the integral of the composite signal and the other half of the value of the secondary signal will be subtracted from the integral during the interval 126, or more properly in those portions of the negative phases of the signal of line 114 preceding and following interval 122 and corresponding in time to intervals 116 and 120 of the signal of line 112.

In the same manner, if the integration is taken according to the intervals 122 and 126 of the secondary signal, the contribution of the primary signal can be made to cancel. Alternatively, once the primary signal contribution as illustrated by line 28 of FIG. 3 is determined as described, the secondary signal contribution as represented by line 130 can be obtained from composite signal 110 by point by point subtraction.

Therefore, microprocessor 40 by the quadrature integration just described arithmetically derives the integral of the absolute value of the primary contribution as shown by line 128 and the secondary contribution as shown by line 130 in FIG. 3. The ratio of the value of these integrals over one cycle is indicative of the gas concentration in sample cell 20. The ratio is a value which is noise free and characterized by common mode rejection of any circuit or output perturbations introduced at any point in the system 22. Thereafter, through conventional software design, schemes for signal averaging, linearizing, automatic zeroing, automatic span or integral gain adjustments, alarm set points and other control and communication functions now known or later devised can be easily accommodated within the system of FIG. 2 to provide a complex response based in whole or in part on the gas concentrations measured by the system from the plurality of optical benches coupled thereto through multiplexer 46.

Turn now to FIG. 4 wherein the basic operation of the software control used in the illustrated embodiment is briefly set forth in context of a flow diagram. Control is effected through a main program 132 and an interrupt program 134. Main program 132 provides for overall system control while interrupt program 134 calculates the integral values described above in connection with FIG. 3. Interrupt program 134 is a timer controlled interrupt and is entered at step 136 every 0.5 milisecond. From step 136, step 138 is entered wherein a channel is selected and the composite signal from detector 26, as shaped by preamplifier 28 and signal processor 30, is latched into sample and hold circuit 48.

The D/A—A/D conversion within circuit 90 then begins. Phase and source driver flags within the programming are then updated at step 140 to insure that the program has proceeded to the appropriate number of half cycle integrating intervals as described in connection with primary and secondary source timing as represented by lines 112 and 114 in FIG. 3. The conversion within circuit 90 is then tested for completion at step 142. If not completed, step 140 is reentered until such time as the conversion within circuit 90 is completed and counter 70 holds a digital value equal to the analog value held within the sample and hold circuit 48. At this time, step 144 is entered and the digital value of the composite signal which is latched into buffer 82 is read by microproessor 40 through bus 86.

Thereafter the decision point 146 is entered and a determination is made whether or not the digital value read lies within a positive primary phase interval such as interval 116 of line 112 in FIG. 3 or whether it lies within a negative interval, such as interval 120 of line 112 of FIG. 3. If the measured point lines within a negative interval, step 148 is entered and the composite signal thus read is subtracted from the accumulated primary energy value stored within microprocessor 40. If, however, the point lies within the positive portion of the primary phase, step 150 is entered and the read value of the composite signal is added to the accumulated stored primary energy value within microprocessor 40.

Thereafter, step 152 is entered and a similar determination is made relative to the secondary signal, namely, a determination is made whether the point read through circuit 90 is read at a time interval during the negative portion 126 of secondary phase 114 of FIG. 3, or whether it is read during the positive interval 122. If read within the negative interval 126, step 154 is entered and the composite signal which is negative is subtracted from the accumulated secondary energy value stored within microprocessor 40. If the measured point lies within positive interval 122, step 156 is entered and the opposite signal is added to the accumulated secondary energy value.

A test is made at step 158 to determine whether or not the end of the single cycle as illustrated by lines 112 and 114 has been reached. If the end of the cycle has been reached, the accumulated primary and secondary energy values are transferred at step 160 to a memory location accessable by the main program and the temporary accumulated values are cleared in preparation for the start of a new cycle. In either case, step 162 is entered wherein register within microprocessor 40 containing the contents desired to be output is loaded into counter 70. The count from counter 70 is made available as an analog signal at output 76 of D/A converter 74. Thereafter, analog output 76 is sampled and held within sample and hold circuit 102 in step 164. Processing control then returns to the main program 132. One half milisecond later, the timer interrupt will again cause entry at step 136 and either the next point of the same cycle will be completed as just described, or the first point of the next cycle will be measured. If the cycle did not end as tested at step 158, microprocessor 40 will have retained the accumulated values of the primary secondary energy value and will continue as described above.

Turn now to consider main program 132. At step 166 a test is made to determine whether a new energy ratio is to be computed. If not, step 166 enters a wait loop and repeatedly tests the phase flags within microprocessor 40 until the flags indicate that a cycle has been completed and an energy ratio can be computed.

The ratio of the accumulated secondary energy to the accumulated primary energy is calculated at step 168. The ratio is then weighted or tared at step 170 for any zero offset known to exist in the system. After zero adjustment the computed ratio is scaled for the appropriate span correction or gain at step 172. Once the ratio is prepared for zero offset and scale span correction, it is linearized through software control in a conventional manner to convert the computed ratio to a percentage gas concentration at step 174. The percentage gas concentration is then transferred to a selected register at step 176 which register is included as part of microprocessor 40. Output buffers 94 and 96 are then updated with the newly computed percentage gas concentration at step 178 for purposes of external control and communication. Thereafter, main programming returns to step 166 to determine whether or not a new energy value has been measured and is available.

It must be understood that any modifications or alterations may be made by those having ordinary skill in the art without departing from the spirit and scope of the invention. For example, although the illustrated embodiment has shown a two channel infrared gas absorption analyzer, and in particular, an analyzer for measuring carbon dioxide percentages in a sample gas, it is to be expected that more than two channels could be accommodated and that a plurality of different types of gasses each corresponding to a separate optical bench, can also be accommodated by extending the teachings of the invention. Therefore, the illustrated embodiment has been shown only for the purposes of example and should not be taken as limiting the invention which is defined in the following claims.

We claim:

1. An apparatus for use in combination with an optical bench for generating an analog composite signal, said analog composite signal comprised of a primary component derived from a reference beam generated by a primary source and a secondary component derived from a sample beam generated by a secondary source, said apparatus comprising:

first means for digitizing said analog composite signal;

second means coupled to said first means, said second means for demodulating said digitized composite signal into a digitized primary component and secondary component; and, third means coupled to said second means, said third means for generating the ratio of said secondary component to said primary component;

whereby common mode rejection within said composite signal is achieved in said apparatus in a digital format.

2. The apparatus of claim 1 wherein said first means for digitizing said analog composite signal comprises:

means for generating a digital count;

means for selectively storing said digital count; and, means for converting said digital count to an analog signal for comparison to said analog composite signal, the difference therebetween being used to revise the value of said digital count until said difference is nulled, said digital count then being coupled to said third means for generation of said ratio of said secondary to primary components.

3. The apparatus of claim 1 wherein said second means for demodulating said composite signal into said primary and secondary components comprises:

means for integrating the absolute value of said primary component and for integrating the absolute value of said secondary component, said primary and secondary components within said composite signal being phase shifted with respect to each other by approximately ninety degrees.

4. The apparatus of claim 1 wherein said second means for demodulating said composite signal into said primary and secondary components comprises:

means for driving said primary source and secondary source approximately ninety degrees apart in phase; and, means for integrating said composite signal to obtain an absolute value of said primary component according to the quadrature of said primary source as determined by said means for driving, and for integrating said composite signal to obtain an absolute value of said secondary component according to the quadrature of said secondary source as determined by said means for driving.

5. The apparatus of claim 4 wherein said means for integrating said composite signal according to said quadrature of said primary source and according to said quadrature of said secondary source integrates said composite signal through one cycle of said primary source and secondary source respectively.

6. A method for determining a percentage concentration of an energy absorbing substance in a sample comprising the steps of:

periodically generating a reference beam of radiant energy from a primary source;

periodically generating a sample beam of radiant energy from a secondary source;

generating an analog composite signal comprised of a primary component derived from exposure of said sample to said reference beam and a secondary component derived from exposure of said sample to said sample beam, the periodic generation of said reference and sample beams being phase shifted with respect to each other by approximately ninety degrees so that said primary and secondary components of said composite signal are similarly phase shifted with respect to each other by approximately ninety degrees;

digitizing said analog composite signal;

integrating said composite signal according to the quadrature of one of said primary and secondary components to obtain the integral of an absolute value of said one component;

deriving the integral of the absolute value of said other one of said primary and secondary components of said composite signal; and, generating the ratio of said integral of the absolute value of said secondary and primary components;

whereby extremely fast and accurate percentage concentration of said energy absorbing substance as determined by said reference beam and sample beam are generated with common mode rejection.

7. The method of claim 6 where said step of deriving said other one of said primary and secondary components of said composite signal comprises the step of integrating said composite signal according to the quadrature of said other one of said primary and secondary components to obtain the integral of the absolute value thereof.

8. The method of claim 6 wherein:

said steps of periodically generating said reference beam, periodically generating said sample beam, integrating according to the quadrature of one of said primary and secondary components of said analog composite signal, deriving the integral of the absolute value of said other one of said primary and secondary components of said composite signal and generating the ratio of said integral of said absolute value of said secondary component to said integral of the absolute value of said primary component are each steps performed within a microprocessor;

said step of digitizing said analog composite signal is performed within a D/A—A/D convertor in communication with said microprocessor; and, said step of generating said reference beam and sample beam is performed in an optical bench coupled to said D/A—A/D convertor and is controlled by said microprocessor.

9. An improvement to the method for generating the relative amount of a predetermined energy absorbing substance in a sample wherein said sample is exposed to a reference beam and a sample beam generated respectively from a primary source and secondary source, a composite signal, having a primary component and secondary component generated by detection of said reference beam and sample beam transmitted through said sample, being digitized and presented for evaluation, said improvement comprising the steps of:

generating said reference beam approximately ninety degrees out of phase with said sample beam; and, integrating said composite signal according to the quadrature of one of said primary and secondary components of said composite signal to obtain the integral of the absolute value of said one component.

10. The improvement of claim 9 further comprising the steps of integrating said composite signal according to the quadrature of the other one of said primary and secondary components of said composite signal to obtain the integral of the absolute value of said other component; and,
generating the ratio of the integral of the absolute value of said secondary component to the integral of the absolute value of said primary component, said ratio being related to the percentage of said specified substance in said sample.

* * * * *